US006936070B1

(12) United States Patent
Muhanna

(10) Patent No.: US 6,936,070 B1
(45) Date of Patent: Aug. 30, 2005

(54) INTERVERTEBRAL DISC PROSTHESIS AND METHODS OF IMPLANTATION

(76) Inventor: Nabil L. Muhanna, 2128 Valley Rd., Gainesville, GA (US) 30501

( * ) Notice: Subject to any disclaimer, the term of this patent is extended or adjusted under 35 U.S.C. 154(b) by 0 days.

(21) Appl. No.: 10/047,587

(22) Filed: Jan. 15, 2002

Related U.S. Application Data

(60) Provisional application No. 60/262,974, filed on Jan. 17, 2001.

(51) Int. Cl.$^7$ ............................................. A61F 2/44
(52) U.S. Cl. ............................ 623/17.12; 623/17.11
(58) Field of Search .......................... 623/17.12, 17.11

(56) References Cited

U.S. PATENT DOCUMENTS

| | | | |
|---|---|---|---|
| 3,875,595 A | | 4/1975 | Froning .............................. 3/1 |
| 4,349,921 A | * | 9/1982 | Kuntz ..................... 623/17.16 |
| 4,863,477 A | * | 9/1989 | Monson ................... 623/17.12 |
| 5,314,477 A | | 5/1994 | Marnay ........................ 623/17 |
| 5,674,296 A | | 10/1997 | Bryan et al. .................. 623/17 |
| 6,096,080 A | | 8/2000 | Nicholson et al. ............ 623/17 |
| 6,140,452 A | | 10/2000 | Felt et al. ...................... 528/60 |
| 6,146,422 A | | 11/2000 | Lawson .................... 623/17.16 |
| 6,187,043 B1 | * | 2/2001 | Ledergerber ................... 623/8 |
| 6,395,032 B1 | * | 5/2002 | Gauchet ................... 623/17.12 |
| 2001/0039458 A1 | * | 11/2001 | Boyer et al. ............. 623/23.63 |

FOREIGN PATENT DOCUMENTS

WO  WO 99/11203  3/1999 ............. A61F 2/44

OTHER PUBLICATIONS

Experience and Short-Term Results with No-React Cardiovascular Implants—Chapter 15—Advances in Anticalcific and Antidegenrative Treatment of Heart Valve Bioprstheses, First Edition, edited by Shlomo Gabbay, M.D., David J. Wheatley, M.D., Silent Partners, Inc, pp. 189-196—1997.
Unsurpassed Cytocompatibility Carotid and Peripheral Vascular Patch—Shelhigh No-React VascuPatch—Shelhigh, Inc. (believed to be known by others prior to Jan. 17, 2001).

(Continued)

Primary Examiner—Cary E. O'Connor
Assistant Examiner—Candice C. Stokes
(74) Attorney, Agent, or Firm—Womble Carlyle Sandridge & Rice, PLLC

(57) ABSTRACT

The present invention provides biocompatible intervertebral disc prostheses that are resilient to compressive forces, that may be adapted to an intervertebral space. When implanted in the spinal column of a patient, the intervertebral disc prostheses according to the present invention is intended to maintain the separation between adjacent vertebrae and provide shock absorbent protection. Flexibility of the spinal column may also be maintained. The present invention further provides methods for the implantation of the intervertebral disc prosthesis of the present invention and an optional intervertebral spacer into the spinal column of a human or animal patient.

17 Claims, 3 Drawing Sheets

OTHER PUBLICATIONS

Shelhigh N-React—Pericardial Patch—Clinical Results—Shelhigh, Inc.—0318 (believed to be known by others prior to Jan. 17, 2001).

Shelhigh DuraShield—No-React Treated, Dural Repair Patch—Shelhigh, Inc.—0318 (believed to be known by others prior to Jan. 17, 2001).

No-React Detoxification Process: A Superior Anticalcification Method for Bioprostheses Abolhoda, M.D. et al.—1996—The Society of Thoracic Surgeons—Published by Elsevier Science, Inc.—pp. 1724-1730—1996.

Calcification of Bovine Pericardium: Glutaraldehyde Versus No-React Biomodiciation—Abolhoda, M.D. et al.—1996—The Society of Thoracic Surgeons—Published by Elsevier Science, Inc.—pp. 169-174—1996.

Construction Factors Influencing The Shelhigh Porcine Bioprosthesis—Chapter 18—Advances in Anticalcific and Antidenerative—Treatment of Heart Valve Bioprotheses, First Edition, edited by Shlomo Gabbay, M.D., David J. Wheatley, M.D., Silent Partners, Inc., pp. 221-231—1997.

Structure of The Human Intervertebral Disk—Diwan et al.—Current Concepts in Intervertebral Disk Restoration—pp. 454-464—2000.

Review—The Artificial Disc: Theory, Design and Materials—Qi-Bin Bao et al.—Biomaterials 1998—pp. 1157-1167—1996.

* cited by examiner

INTERVERTEBRAL DISC PROSTHESIS AND METHODS OF IMPLANTATION

CROSS REFERENCE TO RELATED APPLICATION

This application claims the benefit of Provisional Application No. 60/262,974, filed Jan. 17, 2001.

FIELD OF THE INVENTION

The present invention generally relates to a prosthesis to replace an injured intervertebral disc. The present invention further relates to methods for implanting the intervertebral disc prosthesis into the spinal column.

BACKGROUND OF THE INVENTION

The spinal column, which is the central support to the vertebrate skeleton and a protective enclosure for the spinal cord, is a linear series of bones, or vertebrae. Intervertebral discs separate and reduce friction between adjacent vertebrae and absorb compression forces applied to the spinal column. Spinal nerves that extend from each side of the spinal cord exit the column at intervertebral forama.

A typical vertebra comprises an anterior body, and a posterior arch that surrounds the spinal cord lying within the vertebral foramen formed by the arch. The muscles that flex the spine are attached to three processes extending from the posterior arch. On the upper surface of each vertebra in a standing human are two superior articulated processes that oppose two inferior articulated processes extending from the lower surface of an adjacent vertebra. Facets on the opposing processes determine the range and direction of movement between adjacent vertebrae, and hence the flexibility of the spinal column.

The intervertebral discs include the fibrillar cartilage of the anulus fibrosus, a fibrous ring, the center of which is filled with an elastic fibrogelatinous pulp that acts as a shock absorber. The outer third of the anulus fibrosus is innervated. The entire spinal column is united and strengthened by encapsulating ligaments.

Back pain is one of the most significant problems facing the workforce in the United States today. It is a leading cause of sickness-related absenteeism and is the main cause of disability for people between ages 19 and 45. Published reports suggest that the economic cost is significant, treatment alone exceeding $80 billion annually. Although acute back pain is common and typically treated with analgesics, chronic pain may demand surgery for effective treatment.

Back pain can occur from pinching or irritation of spinal nerves, compression of the spine, vertebral shifting relative to the spinal cord axis, and bone spur formation. The most common cause of disabling back pain, however, stems from trauma to an intervertebral disc, resulting from mechanical shock, stress, tumors or degenerative disease, which may impair functioning of the disc and limit spinal mobility. In many cases, the disc is permanently damaged and the preferred treatment becomes partial or total excision.

Another cause of back injury is herniation of the intervertebral disc, wherein the gelatinous fluid of the nucleus pulposus enters the vertebral canal and pressures the spinal cord. Again, surgery is often the only method available for permanent relief from pain or the neurological damage ensuing from the pressure of fluid on the spinal cord, and requires replacement of the damaged disc.

Traumatic injury to an intervertebral disc that is not removed will frequently promote scar tissue formation. Scar tissue is weaker than original healthy tissue so that the disc will progressively degenerate, lose water content, stiffen and become less effective as a shock absorber. Eventually, the disc may deform, herniate, or collapse, limiting flexibility of the spinal column at that position. The only option is for the intervertebral disc to be partially or totally removed.

When the disc is partially or completely removed, it is necessary to replace the excised material to prevent direct contact between hard bony surfaces of adjacent vertebrae. One vertebral spacer that may be inserted between adjacent vertebrae, according to U.S. Pat. No. 5,989,291 to Ralph et al., includes two opposing plates separated by a belleville washer or a modified belleville washer. The washer provides a restorative force to mimic the natural function of the disc by providing a shock absorber and mobility between adjacent vertebrae. An alternative approach is a "cage" that maintains the space usually occupied by the disc to prevent the vertebrae from collapsing and impinging the nerve roots. However, mechanical devices intended to replicate intervertebral disc function have had only limited success.

Spinal fusion may be used to restrict the motion between two vertebrae that comes from segmental instability. Fusing the vertebrae together, however, reduces the mechanical back pain by preventing the now immobile vertebrae from impinging on the spinal nerve. The disadvantage of such spacers is that stability is created at the expense of the flexibility of the spine.

Surgical procedures for replacing intervertebral disc material, rather than fusing of the vertebrae, have included both anterior approaches and posterior approaches to the spinal column. The posterior approach (from the back of the patient) encounters the spinous process, superior articular process, and the inferior articular process that must be removed to allow insertion of the disc replacement material into the intervertebral space. The anterior approach to the spinal column is complicated by the internal organs that must be bypassed or circumvented to access the vertebrae.

Many intervertebral spacers require preparation of the surfaces of the adjacent vertebrae to accommodate the spacer, causing significant tissue and bone trauma. For example, chiseling or drilling of the vertebral surface may be required to prepare a receiving slot. They may also require screwing the spacer into the intervertebral space, making installation difficult and increasing trauma to the vertebral tissue. Many spacers include complex geometries and are costly to manufacture. Examples of such geometrically complex spacers are described in U.S. Pat. No. 5,609,636 to Kohrs et al., U.S. Pat. No. 5,780,919 to Zdeblick et al., U.S. Pat. No. 5,865,848 to Baker and U.S. Pat. No. 5,776,196 to Matsuzaki et al.

SUMMARY OF THE INVENTION

The present invention provides an intervertebral disc prosthesis that can be inserted relatively easily by the surgeon into the intervertebral space while causing minimal trauma to the opposing surfaces of the vertebrae as well as to the bony processes. The present invention further provides a simple biocompatible spacer that may be implanted into a patient while causing reduced injury to the surrounding tissues and organs.

The present invention provides biocompatible intervertebral disc prostheses that are resilient to compressive forces, that may be adapted to an intervertebral space and when implanted in the spinal column of a patient will maintain the separation between adjacent vertebrae, provide shock absorbent protection and allow flexibility of the spinal column. The present invention further provides methods for the implantation of the intervertebral disc prosthesis of the present invention into the spinal column of a human or animal patient.

One aspect of the present invention, therefore, is an intervertebral disc prosthesis comprising a body adapted to fit an intervertebral space between adjacent vertebrae, wherein the body comprises a resilient biocompatible material. The body of the intervertebral disc prosthesis can be selected from a monolayer sheet, a laminate comprising a plurality of layers, a block, a disc, an annulus and a ribbon. The plurality of layers of the laminate may be fastened to each other by at least one fastener selected from a suture, a staple, a clip, an adhesive or by cell invasion into and between the laminated layers. The intervertebral disc prosthesis is comprised of a resilient biocompatible material selected from a dissected human or animal tissue, an inorganic polymer, an organic polymer, or any combination thereof.

In one aspect of the present invention the intervertebral disc prosthesis is derived from a dissected human or animal pericardium that is fixed by the protein cross-linking agent glutaraldehyde, detoxified and treated with an anti-calcification process. The intervertebral disc prosthesis may further be treated with a blood anti-coagulant.

Another aspect of the present invention is a method of maintaining an intervertebral space between adjacent vertebrae, comprising the steps of excising at least a portion of an intervertebral disc, thereby creating a receiving slot, and inserting into the receiving slot at least one intervertebral disc prosthesis comprising a resilient biocompatible material according to the present invention. The further surgical step of removing a minimal portion of the bony process of a vertebrae to create access to the damaged intervertebral disc may be included in the method of the present invention.

Various other objects, features, and advantages of the invention will become more apparent upon review of the detailed description set forth below when taken in conjunction with the accompanying drawing figures, which are briefly described as follows.

DETAILED DESCRIPTION

Figure 1:
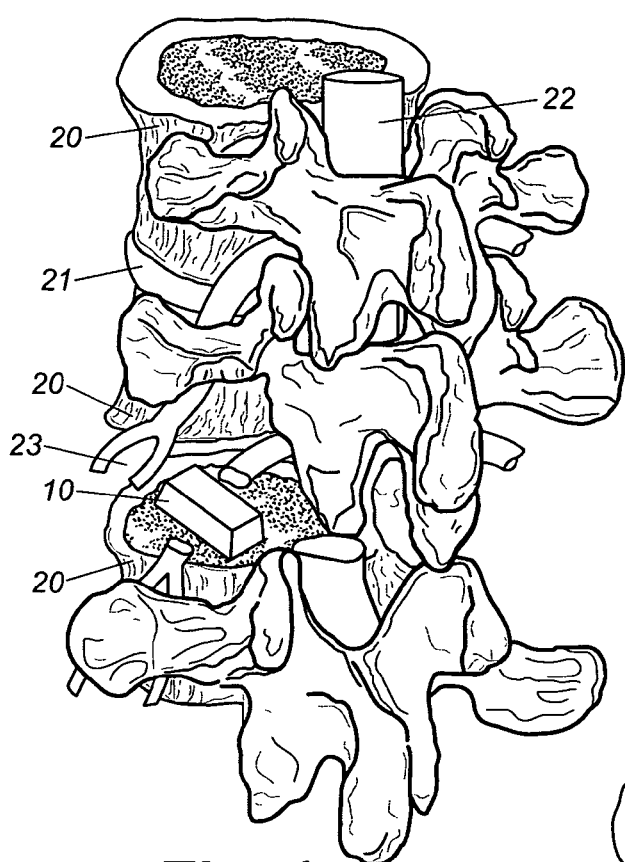
FIG. 1 is an exploded perspective view of a portion of the human spinal column, showing the body of an intervertebral disc prosthesis according to the present invention inserted between adjacent vertebrae.

A full and enabling disclosure of the present invention, including the best mode known to the inventor of carrying out the invention, is set forth more particularly in the remainder of the specification, including reference to the accompanying drawings, wherein like reference numerals designate corresponding parts throughout several figures. This description is made for the purpose of illustrating the general principles of the invention and should not be taken in the limiting sense.

Examples of intervertebral disc prostheses 10 in accordance with the present invention are shown in FIGS. 1–4B. An intervertebral disc prosthesis 10 of the present invention can support adjacent vertebrae 20 after partial or total surgical excision of an intervertebral disc 21. It is contemplated that the intervertebral disc prostheses 10 of the present invention may be used to replace an intervertebral disc 21 that has degenerated due to traumatic injury, vertebral displacement, disease such as, for example, autoimmune disease or rheumatoid arthritis or any other abnormal condition of the spinal column that may injure or shift the intervertebral disc. The intervertebral disc prostheses 10 of the present invention provide support to the vertebrae 20. The resilience of the material selected for use in an intervertebral disc prosthesis 10 provides shock absorbance protection to the spinal cord 22.

The intervertebral disc prosthesis 10 of the present invention includes a body adapted to fit within the intervertebral space 23 between adjacent vertebrae 20. It is intended that the material of the intervertebral disc prosthesis 10 of the present invention is any biocompatible material having a degree of resilience that can provide a level of shock absorbance when the prosthesis is implanted in the spinal column of a patient. It will be understood that a biocompatible material is non-toxic to the tissues of a recipient human or animal patient, and will elicit a non-injurious immune reaction, or is non-immunogenic. A biocompatible material may support the invasion of cells from the recipient patient's own tissues into the intervertebral disc prosthesis 10. Such biocompatible materials may be selected from, but are not limited to, a tissue dissected from a human or animal, a synthetic organic or synthetic inorganic polymer, or any combination thereof. An example of a particularly useful biocompatible tissue is a human or animal pericardium. An example of a biocompatible tissue particularly useful in the present invention is the treated bovine pericardium DURA SHIELD™ (Shelhigh, Inc., Milburn, N.J.). Examples of synthetic materials that are useful in the present invention are GORLEX™ and PROLEAN™.

The dissected tissue that comprises the intervertebral disc prothesis 10 of the present invention may be treated to reduce immunogenicity, which is the ability of an implanted tissue to elicit an immune response in a recipient human or animal. Furthermore, the dissected tissue may be treated with a protein cross-linking agent such as, but not limited to, glutaraldehyde before implantation into the patient.

Any biocompatible tissue may be further treated with an anti-calcification process so that the tissue does not harden, stiffen, or otherwise become brittle after implantation into the intervertebral space or treated with an anti-coagulant such as, but not limited to, heparin.

Any treated biocompatible material for use in an intervertebral disc prosthesis 10 of the present invention may be rendered non-toxic to the recipient patient by a detoxification process, especially, but not only, after treatment of a dissected tissue from a human or animal with a fixing agent. It is also contemplated that the intervertebral disc prostheses 10 of the present invention can be sterilized, before implantation into a patient, by any suitable method known to those skilled in the art and which will not degrade any of the desired mechanical or biological properties of the prosthesis. An example of a method of sterilization and storage of an intervertebral disc prosthesis 10 of the present invention is soaking in benzyl alcohol, which rapidly evaporates before insertion into the patient.

Examples of tissue detoxification and anti-calcification treatment processes, such as the NO-REACT® process (Shelhigh, Inc., Milburn, N.J.), and the design and construction of a detoxified biocompatible tissue such as DURA SHIELD™ (Shelhigh, Inc., Milburn, N.J.) that are suitable materials for the intervertebral disc prosthesis of the present invention are described in Abolhoda et al., Ann. Thoracic Surg. 62, 1724–1730 (1996); Abolhoda et al., Ann. Thoracic Surg. 62, 169–174 (1996); Infantes & Angell. Adv. Anticalcific and Antidegenerative Treatment of Heart Valve Bioprostheses, pp 221–231, ed: Gabbayid S. & Wheatley D. J., pub: Silent Partners, Inc., Austin (1997), which are incorporated herein by reference in their entireties.

In the embodiments of the intervertebral disc prosthesis 10 of the present invention, the body of the intervertebral disc prosthesis 10 may be selected from any geometrical form including, but not limited to, a rectangle, square, circle, and an annulus and which is capable of maintaining the intervertebral space 23 and which will allow mobility and flexibility of the spinal column.

In other embodiments of the present invention, the intervertebral disc prosthesis 10 may further comprise a spacer comprised of a non-resilient biocompatible material selected from the group consisting of a metal such as titanium, a plastic, an inorganic polymer, an organic polymer or a combination thereof. It is contemplated that the spacer may be configured to be compressible, and therefore capable of absorbing compressibility forces applied to the spinal column of the patient.

Figure 2:
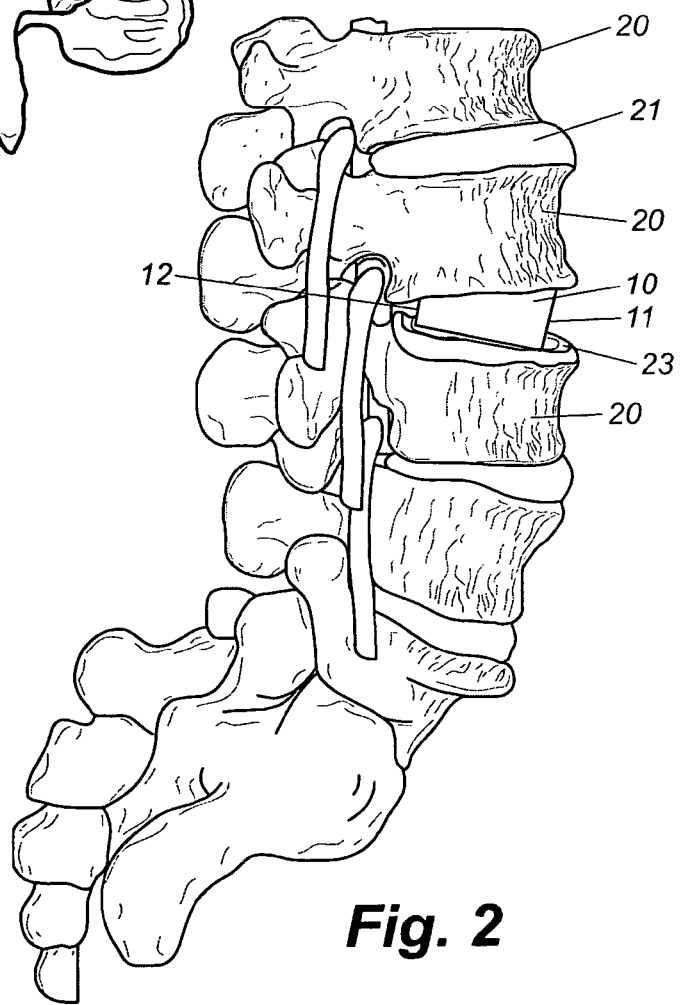
FIG. 2 is a side-elevation of the intervertebral disc prosthesis, shown in FIG. 1, illustrating an intervertebral disc prosthesis inserted between two adjacent vertebrae, wherein an anterior face of the prosthesis is thicker than the posterior face.

In one embodiment of the intervertebral disc prosthesis 10 of the present invention, the intervertebral disc prosthesis 10 has multiple surfaces, including an anterior face 11 and a posterior face 12, wherein the anterior face 11 is directed towards the inner body cavity of the patient, and the posterior face 12 is directed towards the dorsal surface of the patient. The intervertebral disc prosthesis 10 may be configured such that the thickness of the anterior face 11 is greater than the thickness of the posterior face 12, as is illustrated in FIG. 2 or the thickness of the posterior face 12 is greater than the thickness of the anterior face 11. The difference in the thickness of the opposing anterior 11 and posterior 12 faces of the intervertebral disc prosthesis 10 of the present invention may be selected to preserve the natural curvature of the spinal column.

Figure 3A:
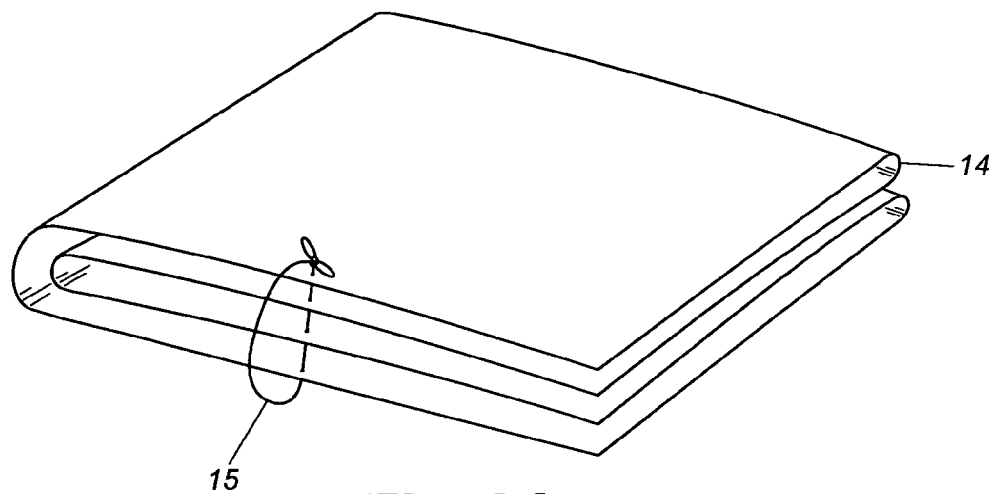
FIG. 3A shows a perspective view illustrating an intervertebral disc prosthesis in the form of a folded sheet of detoxified resilient biocompatible material secured by a suture.
Figure 3B:
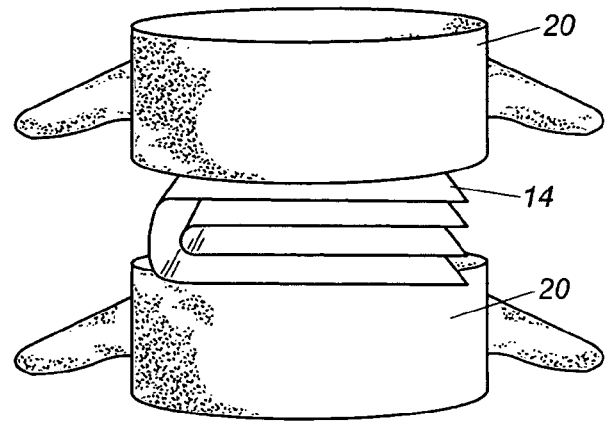
FIG. 3B shows a perspective view of a folded sheet intervertebral disc prosthesis between two adjacent vertebrae as viewed from the front (anterior) of the patient.
Figure 3C:
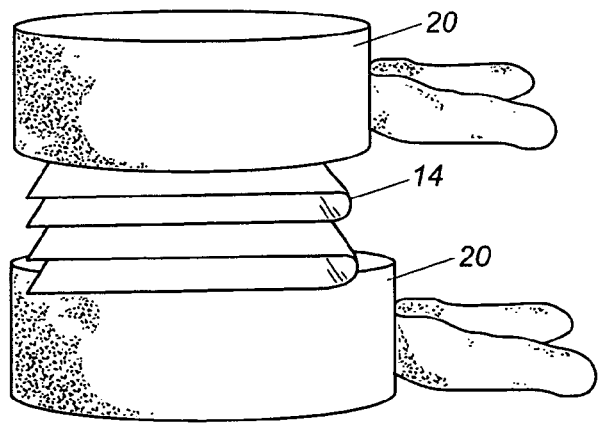
FIG. 3C shows a perspective side-view of a folded sheet intervertebral disc prosthesis between two adjacent vertebrae.

In another embodiment of an intervertebral disc prosthesis 10 of the present invention, the intervertebral disc prosthesis 10 is a folded sheet 14, as shown in FIG. 3A. The sheet 14 can be further adapted, folded or otherwise manipulated to fit within and maintain an intervertebral space 23 between adjacent vertebrae 20, as shown in FIGS. 3B and 3C. The sheet 14 can be secured within the intervertebral space 23 by a first fastener 15 including, but not limited to, a staple, suture, an adhesive, or any other fastening material that can further prevent unfolding of the sheet 14, and which will not significantly impede movement of the vertebrae. Optionally, unfolding of the sheet 14 can be prevented by a first fastener 15 and the prosthesis 10 secured within the intervertebral space 23 by a second fastener 19.

In still another embodiment of an intervertebral disc prosthesis 10 of the present invention, the intervertebral disc prosthesis 10 can be a laminate comprising a purality of layers of the biocompatible material. The plurality of the laminated layers can be secured by a first fastener 15 such as, but not limited to, a staple, a suture, an adhesive, or by fusing the layers together to form the laminate body or cultivating cells within and between the layers, thereby holding the layers in the laminate.

Figure 4A:
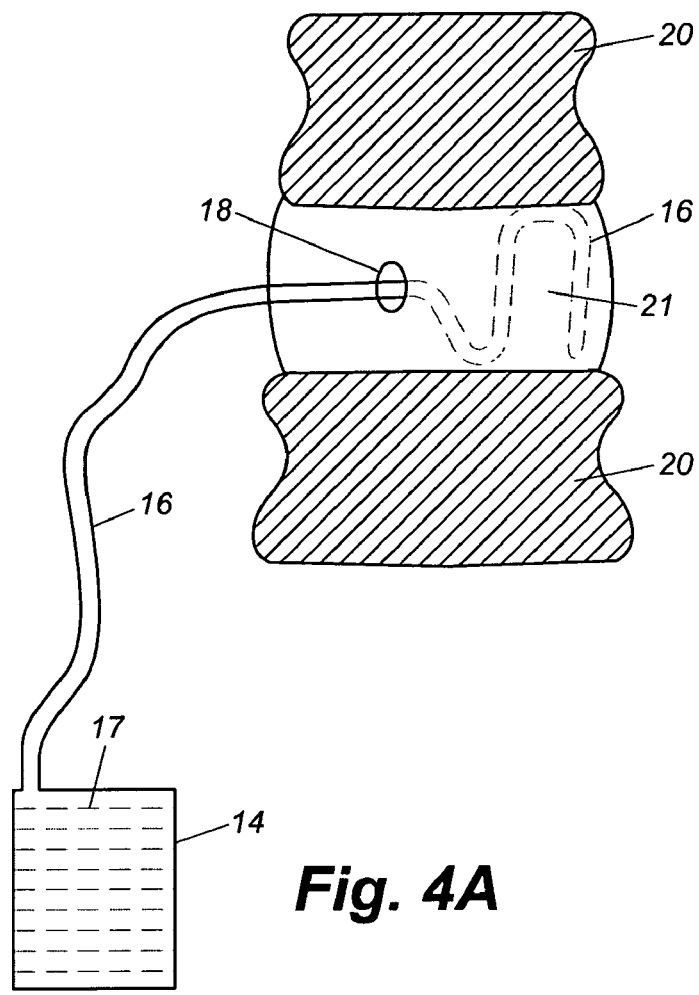
FIG. 4A illustrates the implantation of an intervertebral disc prosthesis, in the form of a ribbon of resilient biocompatible material, into an incision in an intervertebral disc.
Figure 4B:
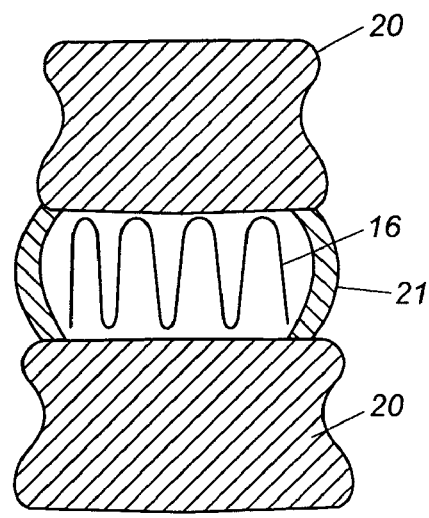
FIG. 4B illustrates a longitudinal section through two adjacent vertebrae and the intervertebral disc and showing, in situ, an intervertebral disc prosthesis, in the form of a ribbon of resilient biocompatible material confined within an intervertebral disc.

In yet another embodiment of intervertebral disc prosthesis 10 of the present invention, as shown in FIG. 4A and FIG. 4B, the intervertebral disc prosthesis 10 is a ribbon 16 of resilient biocompatible material removed from a sheet 14 of the biocompatible material. The sheet 14 of resilient biocompatible material may further comprise at least one predetermined line 17 selected from an indentation, a plurality of indentations or a plurality of partial perforations that can facilitate the removal of the ribbon 16 from the sheet 14. The ribbon 16 of the implantable resilient biocompatible material will allow the surgeon to select the amount of the material to be implanted into an intervertebral space 23, thereby accommodating variations in the size of the intervertebral space 23 in different patients or between different pairs of vertebrae 20. It will further allow the surgeon to insert the material into the intervertebral space 23 with a minimal removal of tissue for access to the implantation site.

In the embodiment illustrated in FIG. 4B, the ribbon 16 may be inserted into the interior of an intervertebral disc 21 that has been hollowed by surgical removal of intervertebral disc tissue or as a result of disc herniation. The ribbon 16 may be inserted through a narrow incision 18 into the intervertebral disc 21 and the ribbon 16 confined therein by the residual intervertebral disc 21.

It is contemplated by the present invention that the biocompatible material of the intervertebral disc prosthesis 10 can be invaded by cells. The proliferating cells may be derived from the patient, or are cells implanted into the intervertebral disc prosthesis before, during, or after implantation into the patient. The cells that can invade an implanted intervertebral disc prosthesis of the present invention include, for example, vascular or neural cells, or chondrocytes. Such cell growth and penetration into an implanted intervertebral disc prosthesis can strengthen the prosthesis and resist slippage of the implant from the intervertebral space.

The present invention further provides a method of using the intervertebral disc prosthesis 10 to maintain the intervertebral space 23. The method of the present invention comprises a surgical procedure for anteriorly or posteriorly installing at least one intervertebral disc prosthesis 10 into an intervertebral space 23 between adjacent vertebrae 20. The intervertebral disc prosthesis 10 can be inserted into the intervertebral space 23 while removing only a portion of the bony process of the adjacent vertebrae 20 so as to minimize trauma to the patient from the surgical procedure. It will be understood by those skilled in the art that the amount of bone removal required for placement of the intervertebral disc prosthesis 10 within an intervertebral space 23 will depend upon the conformation of the vertebrae 20 and spinal column of the individual patient. The intervertebral disc prosthesis 10 can be slid between the adjacent vertebrae 20, thereby minimizing bone removal and reducing the risk of injury to the neural tissue.

The method of the present invention for inserting the intervertebral disc prosthesis 10, as contemplated herein, comprises excising a portion of the intervertebral disc 21 separating adjacent vertebrae 20 thereby creating a receiving slot. The method may further include removing material from at least one vertebra 20. At least one intervertebral disc prosthesis 10 is inserted into the intervertebral space 23 to support and maintain the separation of adjacent vertebrae 20.

The method of the present invention may further comprise the step of implanting an intervertebral spacer between adjacent vertebrae 20. The method of the present invention may also further comprise the step of delivering a substance that, in the intervertebral space 23, will have a consistency ranging from a semi-solid state to a solid state. Examples of suitable substances useful in the present invention include, but are not limited to, a silicone-based polymer, methyl acrylate, a collagen-based gel, or a plastic.

With respect to the above description, it is to be realized that the optimum dimensional relationships for the parts of the invention, to include variations in size, materials, shape, form, function and manner of operation, assembly, and use, are deemed readily apparent and obvious to one skilled in the art, and all equivalent relationships to those illustrated in the drawing and described in the specification are intended to be encompassed by the present invention. Further, the various components of the embodiments of the invention may be interchanged to produce further embodiments and these further embodiments are intended to be encompassed by the present invention.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. An intervertebral disc prosthesis comprising:
    a body adapted to fit an intervertebral space between adjacent vertebrae, wherein the body comprises a resilient biocompatible material; and
    wherein the resilient biocompatible material has at least one defined line for removing a portion of the resilient biocompatible material.

2. The intervertebral disc prosthesis of claim 1, wherein the at least one defined line is selected from a linear indentation, a plurality of indentations or a plurality of perforations.

3. The intervertebral disc prosthesis of claim 1, wherein the portion of the resilient biocompatible material removed is a ribbon.

4. A method of maintaining an intervertebral space between adjacent vertebrae, comprising the steps of:
    (a) excising only a portion of an intervertebral disc, thereby creating a receiving slot in the intervertebral disc; and
    (b) inserting into the receiving slot at least one intervertebral disc prosthesis, the intervertebral disc prosthesis comprising a body adapted to fit an intervertebral space between adjacent vertebrae, wherein the body comprises a resilient, compressible, biocompatible material.

5. An intervertebral disc prosthesis comprising:
    a body adapted to fit an intervertebral space between adjacent vertebrae, wherein the body comprises a resilient biocompatible material; and
    wherein the resilient biocompatible material is treated with a blood anti-coagulant.

6. A method of maintaining an intervertebral space between adjacent vertebrae, comprising the steps of:
    (a) excising at least a portion of an intervertebral disc, thereby creating a receiving slot; and
    (b) inserting into the receiving slot at least one intervertebral disc prosthesis, the intervertebral disc prosthesis comprising a body adapted to fit an intervertebral space between adjacent vertebrae, wherein the body comprises a dissected animal pericardium, and wherein the dissected animal pericardium is detoxified, fixed and treated with an anti-calcification process before implantation into a patient.

7. A method of maintaining an intervertebral space between adjacent vertebrae, comprising the steps of:
    (a) removing a minimal portion of the bony process of a vertebrae, thereby creating access to a damaged intervertebral disc;
    (b) excising only a portion of the intervertebral disc, thereby creating a receiving slot in the intervertebral disc; and
    (c) inserting into the receiving slot at least one intervertebral disc prosthesis, the intervertebral disc prosthesis comprising a body adapted to fit an intervertebral space between adjacent vertebrae, wherein the body comprises a resilient biocompatible material.

8. A method of maintaining an intervertebral space between adjacent vertebrae, comprising the steps of:
    (a) making an incision in an intervertebral disc; and
    (b) inserting a biocompatible material into the interior of the intervertebral disc, the interior of the intervertebral disc being at least partially hollowed out by removal of disc tissue or by disc herniation.

9. The method of claim 8, further comprising removing at least a portion of the intervertebral disc tissue.

10. The method of claim 8, further comprising removing only a portion of the intervertebral disc tissue.

11. The method of claim 8, further comprising selecting the amount of material to be inserted into the interior of the intervertebral disc from a sheet of the biocompatible material.

12. The method of claim 8, wherein the material is a ribbon.

13. The method of claim 8, wherein the material is compressible.

14. The method of claim 8, wherein the material comprises a substance that, when in the interior of the intervertebral disc, has a consistency ranging from a semi-solid state to a solid state.

15. The method of claim 14, wherein the material is selected from the group consisting of a silicone-based polymer, methyl acrylate, a collagen-based gel, and a plastic.

16. A method of maintaining an intervertebral space between adjacent vertebrae, comprising the steps of:
    (a) making an incision in an intervertebral disc;
    (b) selecting an amount of material to be inserted into the interior of the intervertebral disc from a sheet of a biocompatible material, wherein the sheet comprises at least one defined line selected from the group consisting of an indentation, a plurality of indentations, and a plurality of partial perforations; and
    (c) inserting into the interior of the intervertebral disc the biocompatible material.

17. A sheet of biocompatible material for use in an intervertebral disc procedure, the sheet comprising at least one defined line selected from the group consisting of an indentation, a plurality of indentations, and a plurality of partial perforations.

* * * * *

UNITED STATES PATENT AND TRADEMARK OFFICE
Certificate

Patent No. 6,936,070 B1                                                                                              Patented: August 30, 2005

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Nabil L. Muhanna, Gainesville, GA; and David Schalliol, Oakwood, GA.

Signed and Sealed this Twenty-eighth Day of February 2006.

CORRINE M. MCDERMOTT
*Supervisory Patent Examiner*
Art Unit 3738